US006777545B2

(12) United States Patent
Turner, Jr. et al.

(10) Patent No.: US 6,777,545 B2
(45) Date of Patent: Aug. 17, 2004

(54) HUMAN KINASES AND POLYNUCLEOTIDES ENCODING THE SAME

(75) Inventors: C. Alexander Turner, Jr., The Woodlands, TX (US); Brian Mathur, Wooster, OH (US); Carl Johan Friddle, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 115 days.

(21) Appl. No.: 10/116,326

(22) Filed: Apr. 4, 2002

(65) Prior Publication Data

US 2003/0166889 A1 Sep. 4, 2003

Related U.S. Application Data

(60) Provisional application No. 60/282,036, filed on Apr. 6, 2001.

(51) Int. Cl.[7] .......................... C07H 21/04; C12N 1/20; C12N 9/12; C12N 15/00; C12Q 1/68

(52) U.S. Cl. .......................... 536/23.2; 435/194; 435/6; 435/252.3; 435/320.1

(58) Field of Search .................. 435/194, 6, 320.1, 435/252.3; 536/23.2

(56) References Cited

U.S. PATENT DOCUMENTS

| | | |
|---|---|---|
| 4,215,051 A | 7/1980 | Schroeder et al. |
| 4,376,110 A | 3/1983 | David et al. |
| 4,594,595 A | 6/1986 | Struckman |
| 4,631,211 A | 12/1986 | Houghten |
| 4,689,405 A | 8/1987 | Frank et al. |
| 4,713,326 A | 12/1987 | Dattagupta et al. |
| 4,873,191 A | 10/1989 | Wagner et al. |
| 4,946,778 A | 8/1990 | Ladner et al. |
| 5,252,743 A | 10/1993 | Barrett et al. |
| 5,272,057 A | 12/1993 | Smulson et al. |
| 5,424,186 A | 6/1995 | Fodor et al. |
| 5,445,934 A | 8/1995 | Fodor et al. |
| 5,459,127 A | 10/1995 | Felgner et al. |
| 5,556,752 A | 9/1996 | Lockhart et al. |
| 5,700,637 A | 12/1997 | Southern |
| 5,723,323 A | 3/1998 | Kauffman et al. |
| 5,744,305 A | 4/1998 | Fodor et al. |
| 5,756,289 A | 5/1998 | Hoekstra |
| 5,817,479 A | 10/1998 | Au-Young et al. |
| 5,830,721 A | 11/1998 | Stemmer et al. |
| 5,837,458 A | 11/1998 | Minshull et al. |
| 5,869,336 A | 2/1999 | Meyer et al. |
| 5,877,397 A | 3/1999 | Lonberg et al. |
| 5,948,767 A | 9/1999 | Scheule et al. |
| 6,075,181 A | 6/2000 | Kucherlapati et al. |
| 6,110,490 A | 8/2000 | Thierry |
| 6,114,598 A | 9/2000 | Kucherlapati et al. |
| 6,117,679 A | 9/2000 | Stemmer |
| 6,150,584 A | 11/2000 | Kucherlapati et al. |

OTHER PUBLICATIONS

Bird et al, 1988, "Single–Chain Antigen–Binding Proteins", Science 242:423–426.

Bitter et al., 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Cote et al, 1983, "Generation of human monoclonal antibodies reactive with cellular antigens", PNAS USA 80:2026–2030.

Gautier et al, 1987, "α–DNA IV:α–anomeric and β–anomeric tetrathymidylates covalently linked to intercalating oxazolopyridocarbazole. Synthesis, physiochemical properties and poly(rA) binding", Nucleic Acids Research 15(16):6625–6641.

Gordon, 1989, "Transgenic Animals", International Review of Cytology, 115:171–229.

Greenspan et al, 1993, "Idiotypes:structure and immunogenicity", FASEB Journal 7:437–444.

Gu et al, 1994, "Deletion of a DNA Polymerase β Gene Segment in T Cells Using Cell Type–Specific Gene Targeting", Science 265:103–106.

Huse et al, 1989, "Generation of a Large Combinatorial Library of the immunoglobulin Repertoire in Phage Lambda", Science 246:1275–1281.

Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

Inoue et al, 1987, "Sequence–dependent hydrolysis of RNA using modified oligonucleotide splints and R Nase H", FEBS Letters 215(2):327–330.

Inoue et al, 1987, "Synthesis and hybridization studies on two complementary nona(2'–O–methyl)ribonucleotides", Nucleic Acids Research 15(15):6131–6140.

Inouye & Inouye, 1985, "Up–promoter mutations in the lpp gene of *Escherichia coli*", Nucleic Acids Research 13(9):3101–3110.

Janknecht et al, 1991, "Rapid and efficient purification of native histidine–tagged protein expressed by recombinant vaccinia virus", PNAS USA 88:8972–8976.

Kohler & Milstein, 1975, "Continuous cultures of fused cells secreting antibody of predefined specificity", Nature 256:495–497.

Lakso et al, 1992, "Targeted oncogene activation by site–specific recombination in transgenic mice", Proc. Natl. Acad. Sci. USA 89:6232–6236.

Lavitrano et al, 1989, "Sperm Cells as Vectors for Introducing Foreign DNA into Eggs: Genetic Transformation of Mice", Cell 57:717–723.

(List continued on next page.)

Primary Examiner—Maryam Monshipouri

(57) ABSTRACT

Novel human polynucleotide and polypeptide sequences are disclosed that can be used in therapeutic, diagnostic, and pharmacogenomic applications.

5 Claims, No Drawings

OTHER PUBLICATIONS

Lo, 1983, "Transformation by Iontophoretic Microinjection of DNA: Multiple Integrations without Tandem Insertions", Mol. & Cell. Biology 3(10):1803–1814.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984; "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy Identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the *Autographa californica* Nuclear Polyhedrosis Virus Genome: Deletion Mutations within the Polyhedrin Gene", J. Virol 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeirc processed immunoglobulin genes containing mouse variable and human constant region sequences", Nature 314:452–454.

Thompson et al, 1989, "Germ Line Transmission and Expression of a Corrected HPRT Gene Produced by Gene Targeting in Embryonic Stem Cells", Cell 56:313–321.

Van Der Putten et al, 1985, "Efficient insertion of genes into the mouse germ line via retroviral vectors", Proc. Natl. Acad. Sci. USA 82:6148–6152.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell ii.226–232.

Wigler et al, 1980, "Transformation of mammalian cells with an amplifiable dominant–acting gene", Proc. Natl. Acad. Sci. USA 77(6):3567–3570.

Nagase et al. Prediction of the coding sequences of unidentified Human Genes. XX. The complete sequences of 100 new cDNA Clones from Brain which code for Large Proteins in vitro. DNA Res. Apr. 2001, vol. 8, pp. 85–95, entire document.

Database SPTREMBL. No. O60843, Stanchi et al., Putative Serine/threonine kinase (fragment) NCBI_TaxID=9606.01 Aug. 1998, see the attached alignment to SEQ ID NO:2 and 4.

International Search Report.

HUMAN KINASES AND POLYNUCLEOTIDES ENCODING THE SAME

The present application claims the benefit of U.S. Provisional Application No. 60/282,036, which was filed on Apr. 6, 2001, and is herein incorporated by reference in its entirety.

1. INTRODUCTION

The present invention relates to the discovery, identification, and characterization of novel human polynucleotides encoding proteins sharing sequence similarity with animal kinases. The invention encompasses the described polynucleotides, host cell expression systems, the encoded proteins, fusion proteins, polypeptides and peptides, antibodies to the encoded proteins and peptides, and genetically engineered animals that either lack or overexpress the disclosed polynucleotides, antagonists and agonists of the proteins, and other compounds that modulate the expression or activity of the proteins encoded by the disclosed polynucleotides, which can be used for diagnosis, drug screening, clinical trial monitoring, the treatment of diseases and disorders, and cosmetic or nutriceutical applications.

2. BACKGROUND OF THE INVENTION

Kinases mediate the phosphorylation of a wide variety of proteins and compounds in the cell. Along with phosphatases, kinases are involved in a range of regulatory pathways. Given the physiological importance of kinases, they have been subject to intense scrutiny and are proven drug targets.

3. SUMMARY OF THE INVENTION

The present invention relates to the discovery, identification, and characterization of nucleotides that encode novel human proteins and the corresponding amino acid sequences of these proteins. The novel human proteins (NHPs), described for the first time herein, share structural similarity with animal kinases, including, but not limited to, serine-threonine kinases, and carbon catabolite depressing kinases. Accordingly, the described NHPs encode novel kinases having homologues and orthologs across a range of phyla and species.

The novel human polynucleotides described herein encode open reading frames (ORFs) encoding proteins of 778, 762, and 703 amino acids in length (see respectively SEQ ID NOS:2, 4, and 6).

The invention also encompasses agonists and antagonists of the described NHPs, including small molecules, large molecules, mutant NHPs, or portions thereof, that compete with native NHPs, peptides, and antibodies, as well as nucleotide sequences that can be used to inhibit the expression of the described NHPs (e.g., antisense and ribozyme molecules, and open reading frame or regulatory sequence replacement constructs) or to enhance the expression of the described NHPs (e.g., expression constructs that place the described polynucleotide under the control of a strong promoter system), and transgenic animals that express a NHP sequence, or "knock-outs" (which can be conditional) that do not express a functional NHP. Knock-out mice can be produced in several ways, one of which involves the use of mouse embryonic stem cell ("ES cell") lines that contain gene trap mutations in a murine homolog of at least one of the described NHPs. When the unique NHP sequences described in SEQ ID NOS:1–6 are "knocked-out" they provide a method of identifying phenotypic expression of the particular gene, as well as a method of assigning function to previously unknown genes. In addition, animals in which the unique NHP sequences described in SEQ ID NOS:1–6 are "knocked-out" provide a unique source in which to elicit antibodies to homologous and orthologous proteins, which would have been previously viewed by the immune system as "self" and therefore would have failed to elicit significant antibody responses. To these ends, gene trapped knockout ES cells have been generated in murine homologs of the described NHPs.

Additionally, the unique NHP sequences described in SEQ ID NOS:1–6 are useful for the identification of protein coding sequences, and mapping a unique gene to a particular chromosome. These sequences identify biologically verified exon splice junctions, as opposed to splice junctions that may have been bioinformatically predicted from genomic sequence alone. The sequences of the present invention are also useful as additional DNA markers for restriction fragment length polymorphism (RFLP) analysis, and in forensic biology.

Further, the present invention also relates to processes for identifying compounds that modulate, i.e., act as agonists or antagonists of, NHP expression and/or NHP activity that utilize purified preparations of the described NHPs and/or NHP products, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequence of the novel human ORFs encoding the described novel human kinase proteins.

5. DETAILED DESCRIPTION OF THE INVENTION

The NHPs described for the first time herein are novel proteins that are expressed in, inter alia, human cell lines and human brain, pituitary, cerebellum, spinal cord, lymph node, testis, adrenal gland, uterus, mammary gland, rectum, hypothalamus, ovary, fetal kidney, fetal lung, aorta, 6-, 9-, and 12-week old embryos, adenocarcinoma, osteosarcoma, embryonic carcinoma, and normal umbilical vein cells. The described sequences were compiled from sequences available in GENBANK, and cDNAs generated from human adult and fetal brain, pituitary, hypothalamus, testis, and fetus mRNAs (Edge Biosystems, Gaithersburg, Md.) that were identified using primers generated from human genomic DNA.

The present invention encompasses the nucleotides presented in the Sequence Listing, host cells expressing such nucleotides, the expression products of such nucleotides, and: (a) nucleotides that encode mammalian homologs of the described polynucleotides, including the specifically described NHPs, and the NHP products; (b) nucleotides that encode one or more portions of a NHP that correspond to any functional domain(s), and the polypeptide products specified by such nucleotide sequences, including, but not limited to, the novel regions of any active domain(s); (c) isolated nucleotides that encode mutant versions, engineered or naturally occurring, of the described NHPs, in which all or a part of at least one domain is deleted or altered, and the polypeptide products specified by such nucleotide sequences, including, but not limited to, soluble proteins and peptides; (d) nucleotides that encode chimeric fusion proteins containing all or a portion of a coding region of a NHP, or one of its domains (e.g., a receptor/ligand binding domain, accessory protein/self-association domain, etc.) fused to another peptide or polypeptide; or (e) therapeutic or diagnostic derivatives of the described polynucleotides, such as oligonucleotides, antisense polynucleotides, ribozymes, dsRNA, or gene therapy constructs, comprising a sequence first disclosed in the Sequence Listing.

As discussed above, the present invention includes the human DNA sequences presented in the Sequence Listing (and vectors comprising the same), and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel et al., eds., 1989, Current Protocols in Molecular Biology, Vol. I, Green Publishing Associates, Inc., and John Wiley & Sons, Inc., N.Y., at p. 2.10.3) and encodes a functionally equivalent expression product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species, and mutant NHPs, whether naturally occurring or engineered (by site directed mutagenesis, gene shuffling, directed evolution as described in, for example, U.S. Pat. Nos. 5,837,458 or 5,723,323, both of which are herein incorporated by reference). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar to corresponding regions of SEQ ID NOS:1, 3 or 5 (as measured by BLAST sequence comparison analysis using, for example, the GCG sequence analysis package, as described herein, using default parameters).

The invention also includes nucleic acid molecules, preferably DNA molecules, that hybridize to, and are therefore the complements of, the described NHP-encoding polynucleotides. Such hybridization conditions can be highly stringent or less highly stringent, as described herein. In instances where the nucleic acid molecules are deoxyoligonucleotides ("DNA oligos"), such molecules are generally about 16 to about 100 bases long, or about 20 to about 80 bases long, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a microarray or high-throughput "chip" format). Additionally, a series of NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS:1–6 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS:1–6, or an amino acid sequence encoded thereby. Methods for attaching biopolymers to, or synthesizing biopolymers on, solid support matrices, and conducting binding studies thereon, are disclosed in, inter alia, U.S. Pat. Nos. 5,700,637, 5,556,752, 5,744,305, 4,631,211, 5,445,934, 5,252,743, 4,713,326, 5,424,186, and 4,689,405, the disclosures of which are herein incorporated by reference in their entirety.

Addressable arrays comprising sequences first disclosed in SEQ ID NOS:1–6 can be used to identify and characterize the temporal and tissue specific expression of a gene. These addressable arrays incorporate oligonucleotide sequences of sufficient length to confer the required specificity, yet be within the limitations of the production technology. The length of these probes is usually within a range of between about 8 to about 2000 nucleotides. Preferably the probes consist of 60 nucleotides, and more preferably 25 nucleotides, from the sequences first disclosed in SEQ ID NOS:1–6.

For example, a series of NHP oligonucleotide sequences, or the complements thereof, can be used in chip format to represent all or a portion of the described sequences. The oligonucleotides, typically between about 16 to about 40 (or any whole number within the stated range) nucleotides in length, can partially overlap each other, and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing, and proceed in either a sense (5'-to-3') orientation vis-a-vis the described sequence or in an antisense orientation.

Microarray-based analysis allows the discovery of broad patterns of genetic activity, providing new understanding of gene functions, and generating novel and unexpected insight into transcriptional processes and biological mechanisms. The use of addressable arrays comprising sequences first disclosed in SEQ ID NOS:1–6 provides detailed information about transcriptional changes involved in a specific pathway, potentially leading to the identification of novel components, or gene functions that manifest themselves as novel phenotypes.

Probes consisting of sequences first disclosed in SEQ ID NOS:1–6 can also be used in the identification, selection, and validation of novel molecular targets for drug discovery. The use of these unique sequences permits the direct confirmation of drug targets, and recognition of drug dependent changes in gene expression that are modulated through pathways distinct from the intended target of the drug. These unique sequences therefore also have utility in defining and monitoring both drug action and toxicity.

As an example of utility, the sequences first disclosed in SEQ ID NOS:1–6 can be utilized in microarrays, or other assay formats, to screen collections of genetic material from patients who have a particular medical condition. These investigations can also be carried out using the sequences first disclosed in SEQ ID NOS:1–6 in silico, and by comparing previously collected genetic databases and the disclosed sequences using computer software known to those in the art.

Thus the sequences first disclosed in SEQ ID NOS:1–6 can be used to identify mutations associated with a particular disease, and also in diagnostic or prognostic assays.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence, in conjunction with the presence of one or more specific oligonucleotide sequence(s) first disclosed in SEQ ID NOS:1–6. Alternatively, a restriction map specifying the relative positions of restriction endonuclease digestion sites, or various palindromic or other specific oligonucleotide sequences, can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP antisense molecules, useful, for example, in NHP gene regulation and/or as antisense primers in amplification reactions of NHP nucleic acid sequences. With respect to NHP gene regulation, such techniques can be used to regulate biological functions. Further, such sequences can be used as part of ribozyme and/or triple helix sequences that are also useful for NHP gene regulation.

Inhibitory antisense or double stranded oligonucleotides can additionally comprise at least one modified base moiety that is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including, but not limited to, arabinose, 2-fluoroarabinose, xylulose, and hexose.

In yet another embodiment, the antisense oligonucleotide will comprise at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. USA 85:7448–7451), etc.

Low stringency conditions are well-known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Spring Harbor Press, Cold Spring Harbor, N.Y. (and periodic updates thereof), and Ausubel et al., 1989, supra.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

For example, the present sequences can be used in restriction fragment length polymorphism (RFLP) analysis to identify specific individuals. In this technique, an individual's genomic DNA is digested with one or more restriction enzymes, and probed on a Southern blot to yield unique bands for identification (as generally described in U.S. Pat. No. 5,272,057, incorporated herein by reference). In addition, the sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). Actual base sequence information can be used for identification as an accurate alternative to patterns formed by restriction enzyme generated fragments.

Further, a NHP homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, genomic DNA and/or cDNA obtained by reverse transcription of mRNA prepared from, for example, human or non-human cell lines or tissue known to express, or suspected of expressing, an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known to express, or suspected of expressing, a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see, e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known to express, or suspected of expressing, a NHP, in an individual putatively carrying a mutant NHP allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well-known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of carrying, or known to carry, a mutant NHP allele (e.g., a person manifesting a NHP-associated phenotype such as, for example, behavioral disorders, immune disorders, obesity, high blood pressure, etc.), or a cDNA library can be constructed using RNA from a tissue known to express, or suspected of expressing, a mutant NHP allele. A normal NHP gene, or any suitable fragment thereof, can then be labeled and used as a probe to identify the corresponding mutant NHP allele in such libraries. Clones containing mutant NHP sequences can then be purified and subjected to sequence analysis according to methods well-known to those skilled in the art.

Additionally, an expression library can be constructed utilizing cDNA synthesized from, for example, RNA isolated from a tissue known to express, or suspected of expressing, a mutant NHP allele in an individual suspected of carrying, or known to carry, such a mutant allele. In this manner, gene products made by the putatively mutant tissue may be expressed and screened using standard antibody screening techniques in conjunction with antibodies raised against a normal NHP product, as described below (for screening techniques, see, for example, Harlow and Lane, eds., 1988, "Antibodies: A Laboratory Manual", Cold Spring Harbor Press, Cold Spring Harbor, N.Y.).

Additionally, screening can be accomplished by screening with labeled NHP fusion proteins, such as, for example, alkaline phosphatase-NHP or NHP-alkaline phosphatase fusion proteins. In cases where a NHP mutation results in an expression product with altered function (e.g., as a result of a missense or a frameshift mutation), polyclonal antibodies to a NHP are likely to cross-react with a corresponding mutant NHP expression product. Library clones detected via their reaction with such labeled antibodies can be purified and subjected to sequence analysis according to methods well-known in the art.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721, 5,837,458, 6,117,679, and 5,723,323, which are herein incorporated by reference in their entirety.

The invention also encompasses: (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculovirus as described in U.S. Pat. No. 5,869, 336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include, but are not limited to, inducible and non-inducible promoters, enhancers, operators, and other elements known to those skilled in the art that drive and regulate expression. Such regulatory elements include, but are not limited to, the cytomegalovirus (hCMV) immediate early gene, regulatable, viral elements (particularly retroviral LTR promoters), the early or late promoters of SV40 or adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

Where, as in the present instance, some of the described NHP peptides or polypeptides are thought to be cytoplasmic or nuclear proteins (although processed forms or fragments can be secreted or membrane associated), expression systems can be engineered that produce soluble derivatives of a NHP (corresponding to a NHP extracellular and/or intracellular domains, or truncated polypeptides lacking one or more hydrophobic domains) and/or NHP fusion protein products (especially NHP-Ig fusion proteins, i.e., fusions of a NHP domain to an IgFc), NHP antibodies, and anti-idiotypic antibodies (including Fab fragments) that can be used in therapeutic applications. Preferably, the above expression systems are engineered to allow the desired peptide or polypeptide to be recovered from the culture media.

The present invention also encompasses antibodies and anti-idiotypic antibodies (including Fab fragments), antagonists and agonists of a NHP, as well as compounds or nucleotide constructs that inhibit expression of a NHP sequence (transcription factor inhibitors, antisense and ribozyme molecules, or open reading frame sequence or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs, or inappropriately expressed NHPs, for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHP in the body. The use of engineered host cells and/or animals can offer an advantage in that such systems allow not only for the identification of compounds that bind to the endogenous receptor/ligand of a NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of a soluble NHP, a NHP-IgFc fusion protein, or an anti-idiotypic antibody (or its Fab) that mimics the NHP, could activate or effectively antagonize the endogenous NHP or a protein interactive therewith. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules, can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The Nhp Sequences

The cDNA sequences (SEQ ID NOS:1, 3, and 5) and corresponding deduced amino acid sequences (SEQ ID NOS:2, 4, and 6, respectively) of the described NHPs are presented in the Sequence Listing.

Expression analysis has provided evidence that the described NHPs can be expressed in a moderate range of human tissues. In addition to serine-threonine kinases, the described NHPs also share significant similarity to a range of additional kinase families, including kinases associated with signal transduction, from a variety of phyla and species. The genomic locus encoding the described NHPs is apparently encoded on human chromosome 19 (see GENBANK accession no. AC020922). As such, the described sequences are useful, inter alia, for mapping the coding regions of the human genome, and particularly chromosome 19.

Given the physiological importance of protein kinases, they have been subject to intense scrutiny, as exemplified and discussed in U.S. Pat. Nos. 5,756,289 and 5,817,479, herein incorporated by reference in their entirety, which describe uses and utilities that are applicable to the described NHPs.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees, may be used to generate NHP transgenic animals.

Any technique known in the art may be used to introduce a NHP transgene into animals to produce the founder lines of transgenic animals. Such techniques include, but are not limited to, pronuclear microinjection (Hoppe and Wagner, 1989, U.S. Pat. No. 4,873,191); retrovirus-mediated gene transfer into germ lines (Van der Putten et al., 1985, Proc. Natl. Acad. Sci. USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry a NHP transgene in all their cells, as well as animals that carry a transgene in some, but not all their cells, i.e., mosaic animals or somatic cell transgenic animals. A transgene may be integrated as a single transgene, or in concatamers, e.g., head-to-head tandems or head-to-tail tandems. A transgene may also be selectively introduced into and activated in a particular cell-type by following, for example, the teaching of Lasko et al., 1992, Proc. Natl. Acad. Sci. USA 89:6232–6236. The regulatory sequences required for such a cell-type specific activation will depend upon the particular cell-type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell-type, thus inactivating the endogenous NHP gene in only that cell-type, by following, for example, the teaching of Gu et al., 1994, Science 265:103–106. The regulatory sequences required for such a cell-type specific inactivation will depend upon the particular cell-type of interest, and will be apparent to those of skill in the art.

Once transgenic animals have been generated, the expression of the recombinant NHP sequence may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include, but are not limited to, Northern blot analysis of tissue samples obtained from the animal, in situ hybridization analysis, and RT-PCR. Samples of NHP gene-expressing tissue may also be evaluated immunocytochemically using antibodies specific for the NHP transgene product.

The present invention also provides for "knock-in" animals. Knock-in animals are those in which a polynucleotide sequence (i.e., a gene or a cDNA) that the animal does not naturally have in its genome is inserted in such a way that it is expressed. Examples include, but are not limited to, a human gene or cDNA used to replace its murine ortholog in the mouse, a murine cDNA used to replace the murine gene in the mouse, and a human gene or cDNA or murine cDNA that is tagged with a reporter construct used to replace the murine ortholog or gene in the mouse. Such replacements can occur at the locus of the murine ortholog or gene, or at another specific site. Such knock-in animals are useful for the in vivo study, testing and validation of, intra alia, human drug targets, as well as for compounds that are directed at the same, and therapeutic proteins.

5.2 NHPS and NHP Polypeptides

NHPs, NHP polypeptides, NHP peptide fragments, mutated, truncated, or deleted forms of the NHPs, and/or NHP fusion proteins can be prepared for a variety of uses. These uses include, but are not limited to, the generation of antibodies, as reagents in diagnostic assays, for the identification of other cellular gene products related to a NHP, and as reagents in assays for screening for compounds that can be used as pharmaceutical reagents useful in the therapeutic treatment of mental, biological, or medical disorders and diseases. Given the similarity information and expression data, the described NHPs can be targeted (by drugs, oligonucleotides, antibodies, etc.) in order to treat disease, or to therapeutically augment the efficacy of therapeutic agents.

The Sequence Listing discloses the amino acid sequences encoded by the described NHP-encoding polynucleotides. The NHPs display initiator methionines that are present in DNA sequence contexts consistent with eucaryotic translation initiation sites. The NHPs do not display consensus signal sequences, which indicates that they may be cytoplasmic or possibly nuclear proteins, although they may also be secreted or membrane associated (given the presence of several hydrophobic domains).

The NHP amino acid sequences of the invention include the amino acid sequences presented in the Sequence Listing, as well as analogues and derivatives thereof. Further, corresponding NHP homologues from other species are encompassed by the invention. In fact, any NHP protein encoded by the NHP nucleotide sequences described herein are within the scope of the invention, as are any novel polynucleotide sequences encoding all or any novel portion of an amino acid sequence presented in the Sequence Listing. The degenerate nature of the genetic code is well-known, and, accordingly, each amino acid presented in the Sequence Listing is generically representative of the well-known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al., eds., Scientific American Books, New York, N.Y., herein incorporated by reference), are generically representative of all the various permutations and combinations of nucleic acid sequences that can encode such amino acid sequences.

The invention also encompasses proteins that are functionally equivalent to the NHPs encoded by the presently described nucleotide sequences, as judged by any of a number of criteria, including, but not limited to, the ability to bind and modify a NHP substrate, or the ability to effect an identical or complementary downstream pathway, or a change in cellular metabolism (e.g., proteolytic activity, ion flux, phosphorylation, etc.). Such functionally equivalent NHP proteins include, but are not limited to, additions or substitutions of amino acid residues within the amino acid sequence encoded by the NHP nucleotide sequences described herein, but that result in a silent change, thus producing a functionally equivalent expression product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where the NHP peptide or polypeptide can exist, or has been engineered to exist, as a soluble or secreted molecule, the soluble NHP peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well-known to those skilled in the art. However, such engineered host cells themselves may be used in situations where it is important not only to retain the structural and functional characteristics of a NHP, but to assess biological activity, e.g., in certain drug screening assays.

The expression systems that may be used for purposes of the invention include, but are not limited to, microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing NHP nucleotide sequences and promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing a NHP, or for raising antibodies to a NHP, vectors that direct the expression of high levels of fusion protein products that are readily purified may be desirable. Such vectors include, but are not limited to, the E. coli expression vector pUR278 (Ruther et al., 1983, EMBO J. 2:1791), in which a NHP coding sequence may be ligated individually into the vector in-frame with the lacZ coding region so that a fusion protein is produced; pIN vectors (Inouye and Inouye, 1985, Nucleic Acids Res. 13:3101–3109; Van Heeke and Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target expression product can be released from the GST moiety.

In an exemplary insect system, *Autographa californica* nuclear polyhedrosis virus (AcNPV) is used as a vector to express foreign polynucleotide sequences. The virus grows in *Spodoptera frugiperda* cells. A NHP coding sequence can be cloned individually into a non-essential region (for example the polyhedrin gene) of the virus and placed under control of an AcNPV promoter (for example the polyhedrin promoter). Successful insertion of a NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., see Logan and Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, may be provided. Furthermore, the initiation codon should be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol. 153:516–544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the desired modification and processing of the foreign protein expressed. To this end, eukaryotic host cells that possess the cellular machinery for the desired processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the NHP sequences described herein can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then switched to a selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express the NHP product. Such engineered cell lines may be particularly useful in screening and evaluation of compounds that affect the endogenous activity of the NHP product.

A number of selection systems may be used, including, but not limited to, the herpes simplex virus thymidine kinase (Wigler et al., 1977, Cell 11:223), hypoxanthine-guanine phosphoribosyltransferase (Szybalska and Szybalski, 1962, Proc. Natl. Acad. Sci. USA 48:2026), and adenine phosphoribosyltransferase (Lowy et al., 1980, Cell 22:817) genes, which can be employed in tk$^-$, hgprt$^-$ or aprt$^-$ cells, respectively. Also, antimetabolite resistance can be used as the basis of selection for the following genes: dhfr, which confers resistance to methotrexate (Wigler et al., 1980, Proc. Natl. Acad. Sci. USA 77:3567; O'Hare et al., 1981, Proc. Natl. Acad. Sci. USA 78:1527); gpt, which confers resistance to mycophenolic acid (Mulligan and Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

Alternatively, any fusion protein can be readily purified by utilizing an antibody specific for the fusion protein being expressed. Another exemplary system allows for the ready purification of non-denatured fusion proteins expressed in human cell lines (Janknecht et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$. nitriloacetic acid-agarose columns, and histidine-tagged proteins are selectively eluted with imidazole-containing buffers.

Also encompassed by the present invention are fusion proteins that direct a NHP to a target organ and/or facilitate transport across the membrane into the cytosol. Conjugation of NHPs to antibody molecules or their Fab fragments could be used to target cells bearing a particular epitope. Attaching an appropriate signal sequence to a NHP would also transport a NHP to a desired location within the cell. Alternatively targeting of a NHP or its nucleic acid sequence might be achieved using liposome or lipid complex based delivery systems. Such technologies are described in "Liposomes: A Practical Approach", New, R.R.C., ed., Oxford University Press, N.Y., and in U.S. Pat. Nos. 4,594,595, 5,459,127, 5,948,767 and 6,110,490 and their respective disclosures, which are herein incorporated by reference in their entirety. Additionally embodied are novel protein constructs engineered in such a way that they facilitate transport of NHPs to a target site or desired organ, where they cross the cell membrane and/or the nucleus where the NHPs can exert their functional activity. This goal may be achieved by coupling of a NHP to a cytokine or other ligand that provides targeting specificity, and/or to a protein transducing domain (see generally U.S. Provisional Patent Application Ser. Nos. 60/111,701 and 60/056,713, both of which are herein incorporated by reference, for examples of such transducing sequences), to facilitate passage across cellular membranes, and can optionally be engineered to include nuclear localization signals.

Additionally contemplated are oligopeptides that are modeled on an amino acid sequence first described in the Sequence Listing. Such NHP oligopeptides are generally between about 10 to about 100 amino acids long, or between about 16 to about 80 amino acids long, or between about 20 to about 35 amino acids long, or any variation or combination of sizes represented therein that incorporate a contiguous region of sequence first disclosed in the Sequence Listing. Such NHP oligopeptides can be of any length disclosed within the above ranges and can initiate at any amino acid position represented in the Sequence Listing.

The invention also contemplates "substantially isolated" or "substantially pure" proteins or polypeptides. By a substantially isolated or "substantially pure" protein or polypeptide is meant a protein or polypeptide that has been separated from at least some of those components which naturally accompany it. Typically, the protein or polypeptide is substantially isolated or pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially isolated or pure protein or polypeptide may be obtained, for example, by extraction from a natural source, by expression of a recombinant nucleic acid encoding the protein or polypeptide, or by chemically synthesizing the protein or polypeptide.

Purity can be measured by any appropriate method, e.g., column chromatography such as immunoaffinity chromatography using an antibody specific for the protein or polypeptide, polyacrylamide gel electrophoresis, or HPLC analysis. A protein or polypeptide is substantially free of naturally associated components when it is separated from at least some of those contaminants which accompany it in its natural state. Thus, a polypeptide which is chemically synthesized or produced in a cellular system different from the cell from which it naturally originates will be, by definition, substantially free from its naturally associated components. Accordingly, substantially isolated or pure proteins or polypeptides include eukaryotic proteins synthesized in *E. coli*, other prokaryotes, or any other organism in which they do not naturally occur.

5.3 Antibodies to Nhp Products

Antibodies that specifically recognize one or more epitopes of a NHP, epitopes of conserved variants of a NHP, or peptide fragments of a NHP, are also encompassed by the invention. Such antibodies include, but are not limited to, polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention can be used, for example, in the detection of a NHP in a biological sample and may, therefore, be utilized as part of a diagnostic or prognostic technique whereby patients may be tested for abnormal amounts of a NHP. Such antibodies may also be utilized in conjunction with, for example, compound screening schemes for the evaluation of the effect of test compounds on expression and/or activity of a NHP expression product. Additionally, such antibodies can be used in conjunction with gene therapy to, for example, evaluate normal and/or engineered NHP-expressing cells prior to their introduction into a patient. Such antibodies may additionally be used in methods for the inhibition of abnormal NHP activity. Thus, such antibodies may be utilized as a part of treatment methods.

For the production of antibodies, various host animals may be immunized by injection with a NHP, a NHP peptide (e.g., one corresponding to a functional domain of a NHP), truncated NHP polypeptides (NHP in which one or more domains have been deleted), functional equivalents of a NHP, or mutated variants of a NHP. Such host animals may include, but are not limited to, pigs, rabbits, mice, goats, and rats, to name but a few. Various adjuvants may be used to increase the immunological response, depending on the host species, including, but not limited to, Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and/or coupling with molecules such as keyhole limpet hemocyanin, tetanus toxoid, diphtheria toxoid, ovalbumin, cholera toxin, or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique that provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class, including IgG, IgM, IgE, IgA, and IgD, and any subclass thereof. The hybridomas producing the mAbs of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci. USA 81:6851–6855; Neuberger et al., 1984, Nature, 312:604–608; Takeda et al., 1985, Nature, 314:452–454), by splicing the genes from a mouse antibody molecule of appropriate antigen specificity together with genes from a human antibody molecule of appropriate biological activity, can be used. A chimeric antibody is a molecule in which different portions are derived from different animal species, such as those having a variable region derived from a murine mAb and a human immunoglobulin constant region. Such technologies are described in U.S. Pat. Nos. 6,114,598, 6,075,181 and 5,877,397 and their respective disclosures, which are herein incorporated by reference in their entirety. Also encompassed by the present invention is the use of fully humanized monoclonal antibodies, as described in U.S. Pat. No. 6,150,584 and respective disclosures, which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to: F(ab')$_2$ fragments, which can be produced by pepsin digestion of an antibody molecule; and Fab fragments, which can be generated by reducing the disulfide bridges of F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well-known to those skilled in the art (see, e.g., Greenspan and Bona, 1993, FASEB J. 7:437–444; and Nissinoff, 1991, J. Immunol. 147:2429–2438). For example, antibodies that bind to a NHP domain and competitively inhibit the binding of a NHP to its cognate receptor/ligand can be used to generate anti-idiotypes that "mimic" the NHP and, therefore, bind, activate, or neutralize a NHP, NHP receptor, or NHP ligand. Such anti-idiotypic antibodies or Fab fragments of such anti-idiotypes can be used in therapeutic regimens involving a NHP-mediated pathway.

Additionally given the high degree of relatedness of mammalian NHPs, the presently described knock-out mice (having never seen a NHP, and thus never been tolerized to a NHP) have a unique utility, as they can be advantageously applied to the generation of antibodies against the disclosed mammalian NHPs (i.e., a NHP will be immunogenic in NHP knock-out animals).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising a nucleotide sequence encoding the amino acid sequence shown in SEQ ID NO:2.

2. The isolated nucleic acid molecule of claim 1, wherein said nucleic acid molecule comprises the nucleotide sequence of SEQ ID NO:1.

3. A recombinant expression vector comprising a nucleic acid molecule encoding the amino acid sequence shown in SEQ ID NO:2.

4. The recombinant expression vector of claim 3, wherein said nucleic acid molecule comprises the nucleotide sequence of SEQ ID NO:1.

5. A host cell comprising the recombinant expression vector of claim 3.

* * * * *

UNITED STATES PATENT AND TRADEMARK OFFICE
CERTIFICATE OF CORRECTION

PATENT NO. : 6,777,545 B2
DATED : August 17, 2004
INVENTOR(S) : Turner et al.

It is certified that error appears in the above-identified patent and that said Letters Patent is hereby corrected as shown below:

<u>Column 35, line 38 - Column 36, line 39,</u>
Under the table, replace claims 1-4 with the following:

1. An isolated nucleic acid molecule comprising a nucleotide sequence encoding the amino acid sequence shown in SEQ ID NO:4.

2. The isolated nucleic acid molecule of claim 1, wherein said nucleic acid molecule comprises the nucleotide sequence of SEQ ID NO:3.

3. A recombinant expression vector comprising a nucleic acid molecule encoding the amino acid sequence shown in SEQ ID NO:4.

4. The recombinant expression vector of claim 3, wherein said nucleic acid molecule comprises the nucleotide sequence of SEQ ID NO:3.

Signed and Sealed this

Sixth Day of December, 2005

JON W. DUDAS
*Director of the United States Patent and Trademark Office*

SEQUENCE LISTING

<160> NUMBER OF SEQ ID NOS: 6

<210> SEQ ID NO 1
<211> LENGTH: 2337
<212> TYPE: DNA
<213> ORGANISM: homo sapiens

<400> SEQUENCE: 1

| | | | | | |
|---|---|---|---|---|---|
| atgtcgtccg | gggccaagga | gggaggtggg | ggctctcccg | cctaccacct | cccccacccc | 60 |
| caccccacc | caccccagca | cgcccaatat | gtgggcccct | atcggctgga | gaagacgctg | 120 |
| ggcaaaggac | agacagggct | ggttaaactc | ggggtccact | gcatcacggg | tcagaaggtc | 180 |
| gccatcaaga | tcgtgaaccg | ggagaagctg | tcggagtcgg | tgctgatgaa | ggtggagcgg | 240 |
| gagatcgcca | tcctgaagct | catcgaacac | ccacatgtcc | tcaagctcca | cgacgtctac | 300 |
| gagaacaaga | aatatttgta | cctggttctg | gagcacgtct | cggggggtga | gctattcgac | 360 |
| tacctggtaa | agaaggggag | actgacgccc | aaggaggccc | gaaagttctt | ccgccagatt | 420 |
| gtgtctgcgc | tggacttctg | ccacagctac | tccatctgcc | acagagacct | aaagcccgag | 480 |
| aacctgcttt | tggatgagaa | aaacaacatc | cgcattgcag | acttcggcat | ggcgtccctg | 540 |
| caggtggggg | acagcctcct | ggagaccagc | tgcgggtccc | cccattatgc | gtgtccagag | 600 |

-continued

```
gtgattaagg gggaaaaata tgatggccgc cgggcagaca tgtggagctg tggagtcatc    660
ctcttcgccc tgctcgtggg ggctctgccc tttgatgacg acaacctccg ccagctgctg    720
gagaaggtga acggggcgt cttccacatg ccccacttca ttcctccaga ttgccagagc    780
ctcctgaggg gaatgatcga agtggagccc gaaaaaaggc tcagtctgga gcaaattcag    840
aaacatcctt ggtacctagg cgggaaacac gagccagacc cgtgcctgga gccagcccct    900
ggccgccggg tagccatgcg gagcctgcca tccaacggag agctggaccc cgacgtccta    960
gagagcatgg catcactggg ctgcttcagg gaccgcgaga ggctgcatcg cgagctgcgc   1020
agtgaggagg agaaccaaga aaagatgata tattatctgc ttttggatcg aaggagcggg   1080
tatcccagct gtgaggacca ggacctgcct ccccggaatg atgttgaccc ccccggaag    1140
cgtgtggatt ctcccatgct gagccgtcac gggaagcggc gaccagagcg gaagtccatg   1200
gaagtcctga gcatcaccga tgccgggggt ggtggctccc ctgtacccac ccgacgggcc   1260
ttggagatgg cccagcacag ccagagatcc cgtagcgtca gtggagcctc cacgggtctg   1320
tcctccagcc ctctaagcag cccaaggagt ccggtctttt ccttttcacc ggagccgggg   1380
gctggagatg aggctcgagg cggggctcc ccgacttcca aaacgcagac gctgccttct    1440
cggggcccca ggggtggggg cgccggggag cagcccccgc cccccagtgc ccgctccaca   1500
cccctgcccg gccccccagg ctccccgcgc tcctctggcg ggaccccctt gcactcgcct   1560
ctgcacacgc cccgggccag tcccaccggg acccggggga caacaccacc ccccagcccc   1620
ggcggtggcg tcgggggagc cgcctggagg agtcgtctca actccatccg caacagcttc   1680
ctgggctccc ctcgctttca ccggcgcaag atgcaggtcc ctaccgctga ggagatgtcc   1740
agcttgacgc cagagtcctc cccggagctg gcaaaacgct cctggttcgg gaacttcatc   1800
tccttggaca agaagaaaca aatattcctc gtgctaaagg acaaacctct cagcagcatc   1860
aaagcagaca tcgtccatgc ctttctgtcg atccccagcc tgagtcacag tgtgctgtca   1920
cagaccagct tcagggccga gtacaaggcc agtggcggcc cctccgtctt ccaaaagccc   1980
gtccgcttcc aggtggacat cagctcctct gagggtccag agccctcccc gcgacgggac   2040
ggcagcggag gtggtggcat ctactccgtc accttcactc tcatctcggg tcccagccgt   2100
cggttcaagc gagtggtgga gaccatccag gcacagctcc tgagcactca tgaccagccc   2160
tccgtgcagg ccctggcaga cgagaagaac ggggcccaga cccggcctgc tggtgcccca   2220
ccccgaagcc tgcagccccc acccggccgc ccagacccag agctgagcag ctctccccgc   2280
cgaggccccc ccaaggacaa gaagctcctg gccaccaacg ggacccctct gccctga     2337
```

<210> SEQ ID NO 2
<211> LENGTH: 778
<212> TYPE: PRT
<213> ORGANISM: homo sapiens

<400> SEQUENCE: 2

```
Met Ser Ser Gly Ala Lys Glu Gly Gly Gly Ser Pro Ala Tyr His
  1               5                  10                  15

Leu Pro His Pro His Pro His Pro Pro Gln His Ala Gln Tyr Val Gly
                 20                  25                  30

Pro Tyr Arg Leu Glu Lys Thr Leu Gly Lys Gly Gln Thr Gly Leu Val
             35                  40                  45

Lys Leu Gly Val His Cys Ile Thr Gly Gln Lys Val Ala Ile Lys Ile
         50                  55                  60

Val Asn Arg Glu Lys Leu Ser Glu Ser Val Leu Met Lys Val Glu Arg
```

```
                65                   70                   75                   80
        Glu Ile Ala Ile Leu Lys Leu Ile Glu His Pro His Val Leu Lys Leu
                            85                   90                   95
        His Asp Val Tyr Glu Asn Lys Lys Tyr Leu Tyr Leu Val Leu Glu His
                           100                  105                  110
        Val Ser Gly Gly Glu Leu Phe Asp Tyr Leu Val Lys Lys Gly Arg Leu
                           115                  120                  125
        Thr Pro Lys Glu Ala Arg Lys Phe Phe Arg Gln Ile Val Ser Ala Leu
                           130                  135                  140
        Asp Phe Cys His Ser Tyr Ser Ile Cys His Arg Asp Leu Lys Pro Glu
        145                      150                  155                  160
        Asn Leu Leu Asp Glu Lys Asn Asn Ile Arg Ile Ala Asp Phe Gly
                           165                  170                  175
        Met Ala Ser Leu Gln Val Gly Asp Ser Leu Leu Glu Thr Ser Cys Gly
                           180                  185                  190
        Ser Pro His Tyr Ala Cys Pro Glu Val Ile Lys Gly Glu Lys Tyr Asp
                           195                  200                  205
        Gly Arg Arg Ala Asp Met Trp Ser Cys Gly Val Ile Leu Phe Ala Leu
                           210                  215                  220
        Leu Val Gly Ala Leu Pro Phe Asp Asp Asp Asn Leu Arg Gln Leu Leu
        225                      230                  235                  240
        Glu Lys Val Lys Arg Gly Val Phe His Met Pro His Phe Ile Pro Pro
                           245                  250                  255
        Asp Cys Gln Ser Leu Leu Arg Gly Met Ile Glu Val Glu Pro Glu Lys
                           260                  265                  270
        Arg Leu Ser Leu Glu Gln Ile Gln Lys His Pro Trp Tyr Leu Gly Gly
                           275                  280                  285
        Lys His Glu Pro Asp Pro Cys Leu Glu Pro Ala Pro Gly Arg Arg Val
                           290                  295                  300
        Ala Met Arg Ser Leu Pro Ser Asn Gly Glu Leu Asp Pro Asp Val Leu
        305                      310                  315                  320
        Glu Ser Met Ala Ser Leu Gly Cys Phe Arg Asp Arg Glu Arg Leu His
                           325                  330                  335
        Arg Glu Leu Arg Ser Glu Glu Asn Gln Glu Lys Met Ile Tyr Tyr
                           340                  345                  350
        Leu Leu Leu Asp Arg Lys Glu Arg Tyr Pro Ser Cys Glu Asp Gln Asp
                           355                  360                  365
        Leu Pro Pro Arg Asn Asp Val Asp Pro Pro Arg Lys Arg Val Asp Ser
                           370                  375                  380
        Pro Met Leu Ser Arg His Gly Lys Arg Arg Pro Glu Arg Lys Ser Met
        385                      390                  395                  400
        Glu Val Leu Ser Ile Thr Asp Ala Gly Gly Gly Ser Pro Val Pro
                           405                  410                  415
        Thr Arg Arg Ala Leu Glu Met Ala Gln His Ser Gln Arg Ser Arg Ser
                           420                  425                  430
        Val Ser Gly Ala Ser Thr Gly Leu Ser Ser Ser Pro Leu Ser Ser Pro
                           435                  440                  445
        Arg Ser Pro Val Phe Ser Phe Ser Pro Glu Pro Gly Ala Gly Asp Glu
                           450                  455                  460
        Ala Arg Gly Gly Gly Ser Pro Thr Ser Lys Thr Gln Thr Leu Pro Ser
        465                      470                  475                  480
        Arg Gly Pro Arg Gly Gly Ala Gly Glu Gln Pro Pro Pro Ser
                           485                  490                  495
```

Ala Arg Ser Thr Pro Leu Pro Gly Pro Pro Gly Ser Pro Arg Ser Ser
                500                 505                 510

Gly Gly Thr Pro Leu His Ser Pro Leu His Thr Pro Arg Ala Ser Pro
            515                 520                 525

Thr Gly Thr Pro Gly Thr Thr Pro Pro Ser Pro Gly Gly Gly Val
        530                 535                 540

Gly Gly Ala Ala Trp Arg Ser Arg Leu Asn Ser Ile Arg Asn Ser Phe
545                 550                 555                 560

Leu Gly Ser Pro Arg Phe His Arg Arg Lys Met Gln Val Pro Thr Ala
                565                 570                 575

Glu Glu Met Ser Ser Leu Thr Pro Glu Ser Ser Pro Glu Leu Ala Lys
            580                 585                 590

Arg Ser Trp Phe Gly Asn Phe Ile Ser Leu Asp Lys Glu Glu Gln Ile
        595                 600                 605

Phe Leu Val Leu Lys Asp Lys Pro Leu Ser Ser Ile Lys Ala Asp Ile
    610                 615                 620

Val His Ala Phe Leu Ser Ile Pro Ser Leu Ser His Ser Val Leu Ser
625                 630                 635                 640

Gln Thr Ser Phe Arg Ala Glu Tyr Lys Ala Ser Gly Gly Pro Ser Val
                645                 650                 655

Phe Gln Lys Pro Val Arg Phe Gln Val Asp Ile Ser Ser Glu Gly
            660                 665                 670

Pro Glu Pro Ser Pro Arg Arg Asp Gly Ser Gly Gly Gly Ile Tyr
        675                 680                 685

Ser Val Thr Phe Thr Leu Ile Ser Gly Pro Ser Arg Arg Phe Lys Arg
    690                 695                 700

Val Val Glu Thr Ile Gln Ala Gln Leu Leu Ser Thr His Asp Gln Pro
705                 710                 715                 720

Ser Val Gln Ala Leu Ala Asp Glu Lys Asn Gly Ala Gln Thr Arg Pro
                725                 730                 735

Ala Gly Ala Pro Pro Arg Ser Leu Gln Pro Pro Gly Arg Pro Asp
            740                 745                 750

Pro Glu Leu Ser Ser Ser Pro Arg Arg Gly Pro Pro Lys Asp Lys Lys
        755                 760                 765

Leu Leu Ala Thr Asn Gly Thr Pro Leu Pro
    770                 775

<210> SEQ ID NO 3
<211> LENGTH: 2289
<212> TYPE: DNA
<213> ORGANISM: homo sapiens

<400> SEQUENCE: 3
atgggacttg agtttggttt cctagaggct ggtggaaact ggagtcactt cctcccaggg    60
agtgatggga actggaatct cttcctccca ggaattaatg gaaactggag tctcttcctc   120
ccagggaccc atgggaattg gagtctcttt ctcccaagga tcatgggaat tggagttctc   180
tgccaccagg agccagtgga agtgggagac gaggcccttt ggtcctccac atgcccttc    240 cagccctctg cccctctat atcctttagg tacctggttc tggagcacgt ctcgggggt    300 gagctattcg actacctggt aaagaagggg agactgacgc ccaaggaggc ccgaaagttc   360
ttccgccaga ttgtgtctgc gctggacttc tgccacagct actccatctg ccacagagac   420
ctaaagcccg agaacctgct tttggatgag aaaaacaaca tccgcattgc agacttcggc   480

| | |
|---|---:|
| atggcgtccc tgcaggtggg ggacagcctc ctggagacca gctgcgggtc cccccattat | 540 |
| gcgtgtccag aggtgattaa gggggaaaaa tatgatggcc gccgggcaga catgtggagc | 600 |
| tgtggagtca tcctcttcgc cctgctcgtg ggggctctgc cctttgatga cgacaacctc | 660 |
| cgccagctgc tggagaaggt gaaacggggc gtcttccaca tgccccactt cattcctcca | 720 |
| gattgccaga gcctcctgag gggaatgatc gaagtggagc ccgaaaaaag gctcagtctg | 780 |
| gagcaaattc agaaacatcc ttggtaccta ggcgggaaac acgagccaga cccgtgcctg | 840 |
| gagccagccc ctggccgccg gtagccatg cggagcctgc catccaacgg agagctggac | 900 |
| cccgacgtcc tagagagcat ggcatcactg gctgcttca gggaccgcga gaggctgcat | 960 |
| cgcgagctgc gcagtgagga ggagaaccaa gaaagatga tatattatct gcttttggat | 1020 |
| cggaaggagc ggtatcccag ctgtgaggac caggacctgc ctccccggaa tgatgttgac | 1080 |
| cccccccgga agcgtgtgga ttctcccatg ctgagccgtc acgggaagcg gcgaccagag | 1140 |
| cggaagtcca tggaagtcct gagcatcacc gatgccgggg tggtggctc ccctgtaccc | 1200 |
| acccgacggg ccttggagat ggcccagcac agccagagat cccgtagcgt cagtggagcc | 1260 |
| tccacgggtc tgtcctccag ccctctaagc agcccaagga gtccggtctt ttcctttca | 1320 |
| ccggagccgg gggctggaga tgaggctcga ggcgggggct ccccgacttc aaaacgcag | 1380 |
| acgctgcctt ctcggggccc caggggtggg ggcgccgggg agcagccccc gccccccagt | 1440 |
| gcccgctcca caccctgcc cggcccccca ggctccccgc gctcctctgg cgggacccc | 1500 |
| ttgcactcgc ctctgcacac gccccgggcc agtcccaccg ggaccccggg gacaacacca | 1560 |
| ccccccagcc ccggcggtgg cgtcggggga gccgcctgga ggagtcgtct caactccatc | 1620 |
| cgcaacagct tcctgggctc ccctcgcttt caccggcgca agatgcaggt ccctaccgct | 1680 |
| gaggagatgt ccagcttgac gccagagtcc tccccggagc tggcaaaacg ctcctggttc | 1740 |
| gggaacttca tctccttgga caagaagaa caaatattcc tcgtgctaaa ggacaaacct | 1800 |
| ctcagcagca tcaaagcaga catcgtccat gcctttctgt cgatccccag cctgagtcac | 1860 |
| agtgtgctgt cacagaccag cttcagggcc gagtacaagg ccagtggcgg ccctccgtc | 1920 |
| ttccaaaagc ccgtccgctt ccaggtggac atcagctcct ctgagggtcc agagccctcc | 1980 |
| ccgcgacggg acggcagcgg aggtggtggc atctactccg tcaccttcac tctcatctcg | 2040 |
| ggtcccagcc gtcggttcaa gcgagtggtg agaccatcc aggcacagct cctgagcact | 2100 |
| catgaccagc cctccgtgca ggccctggca gacgagaaga acggggccca gacccggcct | 2160 |
| gctggtgccc caccccgaag cctgcagccc ccacccggcc gcccagaccc agagctgagc | 2220 |
| agctctcccc gccgaggccc cccaaggac aagaagctcc tggccaccaa cgggaccct | 2280 |
| ctgccctga | 2289 |

<210> SEQ ID NO 4
<211> LENGTH: 762
<212> TYPE: PRT
<213> ORGANISM: homo sapiens

<400> SEQUENCE: 4

```
Met Gly Leu Glu Phe Gly Phe Leu Glu Ala Gly Gly Asn Trp Ser His
 1               5                  10                  15

Phe Leu Pro Gly Ser Asp Gly Asn Trp Asn Leu Phe Leu Pro Gly Ile
             20                  25                  30

Asn Gly Asn Trp Ser Leu Phe Leu Pro Gly Thr His Gly Asn Trp Ser
         35                  40                  45
```

-continued

Leu Phe Leu Pro Arg Ile Met Gly Ile Gly Val Leu Cys His Gln Glu
 50                  55                  60

Pro Val Glu Val Gly Asp Glu Ala Leu Trp Ser Ser Thr Cys Pro Phe
 65                      70                  75                  80

Gln Pro Ser Ala Pro Ser Ile Ser Phe Arg Tyr Leu Val Leu Glu His
                 85                  90                  95

Val Ser Gly Gly Glu Leu Phe Asp Tyr Leu Val Lys Lys Gly Arg Leu
                100                 105                 110

Thr Pro Lys Glu Ala Arg Lys Phe Phe Arg Gln Ile Val Ser Ala Leu
            115                 120                 125

Asp Phe Cys His Ser Tyr Ser Ile Cys His Arg Asp Leu Lys Pro Glu
        130                 135                 140

Asn Leu Leu Asp Glu Lys Asn Asn Ile Arg Ile Ala Asp Phe Gly
145                 150                 155                 160

Met Ala Ser Leu Gln Val Gly Asp Ser Leu Leu Glu Thr Ser Cys Gly
                165                 170                 175

Ser Pro His Tyr Ala Cys Pro Glu Val Ile Lys Gly Glu Lys Tyr Asp
                180                 185                 190

Gly Arg Arg Ala Asp Met Trp Ser Cys Gly Val Ile Leu Phe Ala Leu
            195                 200                 205

Leu Val Gly Ala Leu Pro Phe Asp Asp Asp Asn Leu Arg Gln Leu Leu
210                 215                 220

Glu Lys Val Lys Arg Gly Val Phe His Met Pro His Phe Ile Pro Pro
225                 230                 235                 240

Asp Cys Gln Ser Leu Leu Arg Gly Met Ile Glu Val Glu Pro Glu Lys
                245                 250                 255

Arg Leu Ser Leu Glu Gln Ile Gln Lys His Pro Trp Tyr Leu Gly Gly
            260                 265                 270

Lys His Glu Pro Asp Pro Cys Leu Glu Pro Ala Pro Gly Arg Arg Val
        275                 280                 285

Ala Met Arg Ser Leu Pro Ser Asn Gly Glu Leu Asp Pro Asp Val Leu
290                 295                 300

Glu Ser Met Ala Ser Leu Gly Cys Phe Arg Asp Arg Glu Arg Leu His
305                 310                 315                 320

Arg Glu Leu Arg Ser Glu Glu Asn Gln Glu Lys Met Ile Tyr Tyr
            325                 330                 335

Leu Leu Leu Asp Arg Lys Glu Arg Tyr Pro Ser Cys Glu Asp Gln Asp
            340                 345                 350

Leu Pro Pro Arg Asn Asp Val Asp Pro Pro Arg Lys Arg Val Asp Ser
        355                 360                 365

Pro Met Leu Ser Arg His Gly Lys Arg Pro Glu Arg Lys Ser Met
370                 375                 380

Glu Val Leu Ser Ile Thr Asp Ala Gly Gly Gly Ser Pro Val Pro
385                 390                 395                 400

Thr Arg Arg Ala Leu Glu Met Ala Gln His Ser Gln Arg Ser Arg Ser
            405                 410                 415

Val Ser Gly Ala Ser Thr Gly Leu Ser Ser Pro Leu Ser Ser Pro
                420                 425                 430

Arg Ser Pro Val Phe Ser Phe Ser Pro Glu Pro Gly Ala Gly Asp Glu
        435                 440                 445

Ala Arg Gly Gly Gly Ser Pro Thr Ser Lys Thr Gln Thr Leu Pro Ser
450                 455                 460

Arg Gly Pro Arg Gly Gly Gly Ala Gly Glu Gln Pro Pro Pro Pro Ser

| | | | |
|---|---|---|---|
| 465 | 470 | 475 | 480 |

Ala Arg Ser Thr Pro Leu Pro Gly Pro Pro Gly Ser Pro Arg Ser Ser
            485                 490                 495

Gly Gly Thr Pro Leu His Ser Pro Leu His Thr Pro Arg Ala Ser Pro
            500                 505                 510

Thr Gly Thr Pro Gly Thr Thr Pro Pro Ser Pro Gly Gly Gly Val
            515                 520                 525

Gly Gly Ala Ala Trp Arg Ser Arg Leu Asn Ser Ile Arg Asn Ser Phe
            530                 535                 540

Leu Gly Ser Pro Arg Phe His Arg Arg Lys Met Gln Val Pro Thr Ala
545                 550                 555                 560

Glu Glu Met Ser Ser Leu Thr Pro Glu Ser Ser Pro Glu Leu Ala Lys
            565                 570                 575

Arg Ser Trp Phe Gly Asn Phe Ile Ser Leu Asp Lys Glu Glu Gln Ile
            580                 585                 590

Phe Leu Val Leu Lys Asp Lys Pro Leu Ser Ser Ile Lys Ala Asp Ile
            595                 600                 605

Val His Ala Phe Leu Ser Ile Pro Ser Leu Ser His Ser Val Leu Ser
            610                 615                 620

Gln Thr Ser Phe Arg Ala Glu Tyr Lys Ala Ser Gly Gly Pro Ser Val
625                 630                 635                 640

Phe Gln Lys Pro Val Arg Phe Gln Val Asp Ile Ser Ser Ser Glu Gly
            645                 650                 655

Pro Glu Pro Ser Pro Arg Arg Asp Gly Ser Gly Gly Gly Ile Tyr
            660                 665                 670

Ser Val Thr Phe Thr Leu Ile Ser Gly Pro Ser Arg Arg Phe Lys Arg
            675                 680                 685

Val Val Glu Thr Ile Gln Ala Gln Leu Leu Ser Thr His Asp Gln Pro
            690                 695                 700

Ser Val Gln Ala Leu Ala Asp Glu Lys Asn Gly Ala Gln Thr Arg Pro
705                 710                 715                 720

Ala Gly Ala Pro Pro Arg Ser Leu Gln Pro Pro Gly Arg Pro Asp
            725                 730                 735

Pro Glu Leu Ser Ser Ser Pro Arg Arg Gly Pro Pro Lys Asp Lys Lys
            740                 745                 750

Leu Leu Ala Thr Asn Gly Thr Pro Leu Pro
            755                 760

<210> SEQ ID NO 5
<211> LENGTH: 2112
<212> TYPE: DNA
<213> ORGANISM: homo sapiens

<400> SEQUENCE: 5

| | | |
|---|---|---|
| atgaaggtgg agcgggagat cgccatcctg aagctcatcg aacacccaca tgtcctcaag | 60 |
| ctccacgacg tctacgagaa caagaaatat ttgtacctgg ttctggagca cgtctcgggg | 120 |
| ggtgagctat tcgactacct ggtaaagaag gggagactga cgcccaagga ggcccgaaag | 180 |
| ttcttccgcc agattgtgtc tgcgctggac ttctgccaca gctactccat ctgccacaga | 240 |
| gacctaaagc ccgagaacct gcttttggat gagaaaaaca catccgcat gcagacttc | 300 |
| ggcatggcgt ccctgcaggt gggggacagc ctcctggaga ccagctgcgg gtcccccat | 360 |
| tatgcgtgtc cagaggtgat taaggggaa aaatatgatg ccgccgggc agacatgtgg | 420 |
| agctgtggag tcatcctctt cgccctgctc gtggggctc tgccctttga tgacgacaac | 480 |

-continued

```
ctccgccagc tgctggagaa ggtgaaacgg ggcgtcttcc acatgcccca cttcattcct    540
ccagattgcc agagcctcct gagggaatg atcgaagtgg agcccgaaaa aaggctcagt    600
ctggagcaaa ttcagaaaca tccttggtac ctaggcggga acacgagcc agacccgtgc    660 ctggagccag cccctggccg ccgggtagcc atgcggagcc tgccatccaa cggagagctg    720
gaccccgacg tcctagagag catggcatca ctgggctgct tcagggaccg cgagaggctg    780
catcgcgagc tgcgcagtga ggaggagaac caagaaaaga tgatatatta tctgcttttg    840
gatcggaagg agcggtatcc cagctgtgag gaccaggacc tgcctccccg gaatgatgtt    900
gacccccccc ggaagcgtgt ggattctccc atgctgagcc gtcacgggaa gcggcgacca    960
gagcggaagt ccatggaagt cctgagcatc accgatgccg ggggtggtgg ctcccctgta   1020
cccacccgac gggccttgga gatggcccag cacagccaga gatcccgtag cgtcagtgga   1080
gcctccacgg gtctgtcctc cagccctcta agcagcccaa ggagtccggt ctttccttt    1140 tcaccggagc cggggctgg agatgaggct cgaggcgggg gctccccgac ttccaaaacg   1200
cagacgctgc cttctcgggg ccccagggg ggggcgccg gggagcagcc ccgccccc     1260 agtgcccgct ccacacccct gcccggcccc ccaggctccc cgcgctcctc tggcgggacc   1320
cccttgcact cgcctctgca cacgcccgg gccagtccca ccgggacccc ggggacaaca   1380 ccaccccca gccccggcgg tggcgtcggg ggagccgcct ggaggagtcg tctcaactcc   1440
atccgcaaca gcttcctggg ctcccctcgc tttcaccggc gcaagatgca ggtccctacc   1500
gctgaggaga tgtccagctt gacgccagag tcctccccgg agctggcaaa acgctcctgg   1560
ttcgggaact tcatctcctt ggacaaagaa gaacaaatat tcctcgtgct aaaggacaaa   1620
cctctcagca gcatcaaagc agacatcgtc catgcctttc tgtcgatccc cagcctgagt   1680
cacagtgtgc tgtcacagac cagcttcagg gccgagtaca aggccagtgg cggcccctcc   1740
gtcttccaaa agcccgtccg cttccaggtg gacatcagct cctctgaggg tccagagccc   1800
tccccgcgac gggacggcag cggaggtggt ggcatctact ccgtcacctt cactctcatc   1860
tcgggtccca gccgtcggtt caagcgagtg gtggagacca tccaggcaca gctcctgagc   1920
actcatgacc agccctccgt gcaggccctg gcagacgaga gaacggggc ccagacccgg   1980 cctgctggtg ccccaccccg aagcctgcag ccccaccccg gccgcccaga cccagagctg   2040
agcagctctc cccgccgagg cccccccaag gacaagaagc tcctggccac caacgggacc   2100
cctctgccct ga                                                        2112
```

<210> SEQ ID NO 6
<211> LENGTH: 703
<212> TYPE: PRT
<213> ORGANISM: homo sapiens

<400> SEQUENCE: 6

```
Met Lys Val Glu Arg Glu Ile Ala Ile Leu Lys Leu Ile Glu His Pro
  1               5                  10                  15

His Val Leu Lys Leu His Asp Val Tyr Glu Asn Lys Lys Tyr Leu Tyr
             20                  25                  30

Leu Val Leu Glu His Val Ser Gly Gly Glu Leu Phe Asp Tyr Leu Val
         35                  40                  45

Lys Lys Gly Arg Leu Thr Pro Lys Glu Ala Arg Lys Phe Phe Arg Gln
     50                  55                  60

Ile Val Ser Ala Leu Asp Phe Cys His Ser Tyr Ser Ile Cys His Arg
 65                  70                  75                  80
```

-continued

```
Asp Leu Lys Pro Glu Asn Leu Leu Asp Glu Lys Asn Asn Ile Arg
            85                  90                  95
Ile Ala Asp Phe Gly Met Ala Ser Leu Gln Val Gly Asp Ser Leu Leu
            100                 105                 110
Glu Thr Ser Cys Gly Ser Pro His Tyr Ala Cys Pro Glu Val Ile Lys
            115                 120                 125
Gly Glu Lys Tyr Asp Gly Arg Arg Ala Asp Met Trp Ser Cys Gly Val
    130                 135                 140
Ile Leu Phe Ala Leu Leu Val Gly Ala Leu Pro Phe Asp Asp Asp Asn
145                 150                 155                 160
Leu Arg Gln Leu Leu Glu Lys Val Lys Arg Gly Val Phe His Met Pro
                165                 170                 175
His Phe Ile Pro Pro Asp Cys Gln Ser Leu Leu Arg Gly Met Ile Glu
            180                 185                 190
Val Glu Pro Glu Lys Arg Leu Ser Leu Glu Gln Ile Gln Lys His Pro
            195                 200                 205
Trp Tyr Leu Gly Gly Lys His Glu Pro Asp Pro Cys Leu Glu Pro Ala
    210                 215                 220
Pro Gly Arg Arg Val Ala Met Arg Ser Leu Pro Ser Asn Gly Glu Leu
225                 230                 235                 240
Asp Pro Asp Val Leu Glu Ser Met Ala Ser Leu Gly Cys Phe Arg Asp
                245                 250                 255
Arg Glu Arg Leu His Arg Glu Leu Arg Ser Glu Glu Asn Gln Glu
            260                 265                 270
Lys Met Ile Tyr Tyr Leu Leu Leu Asp Arg Lys Glu Arg Tyr Pro Ser
    275                 280                 285
Cys Glu Asp Gln Asp Leu Pro Pro Arg Asn Asp Val Asp Pro Pro Arg
    290                 295                 300
Lys Arg Val Asp Ser Pro Met Leu Ser Arg His Gly Lys Arg Arg Pro
305                 310                 315                 320
Glu Arg Lys Ser Met Glu Val Leu Ser Ile Thr Asp Ala Gly Gly Gly
                325                 330                 335
Gly Ser Pro Val Pro Thr Arg Arg Ala Leu Glu Met Ala Gln His Ser
            340                 345                 350
Gln Arg Ser Arg Ser Val Ser Gly Ala Ser Thr Gly Leu Ser Ser Ser
    355                 360                 365
Pro Leu Ser Ser Pro Arg Ser Pro Val Phe Ser Phe Ser Pro Glu Pro
    370                 375                 380
Gly Ala Gly Asp Glu Ala Arg Gly Gly Gly Ser Pro Thr Ser Lys Thr
385                 390                 395                 400
Gln Thr Leu Pro Ser Arg Gly Pro Arg Gly Gly Ala Gly Glu Gln
                405                 410                 415
Pro Pro Pro Pro Ser Ala Arg Ser Thr Pro Leu Pro Gly Pro Pro Gly
            420                 425                 430
Ser Pro Arg Ser Ser Gly Gly Thr Pro Leu His Ser Pro Leu His Thr
    435                 440                 445
Pro Arg Ala Ser Pro Thr Gly Thr Pro Gly Thr Thr Pro Pro Pro Ser
    450                 455                 460
Pro Gly Gly Gly Val Gly Gly Ala Ala Trp Arg Ser Arg Leu Asn Ser
465                 470                 475                 480
Ile Arg Asn Ser Phe Leu Gly Ser Pro Arg Phe His Arg Arg Lys Met
                485                 490                 495
```

-continued

```
Gln Val Pro Thr Ala Glu Glu Met Ser Ser Leu Thr Pro Glu Ser Ser
            500                 505                 510

Pro Glu Leu Ala Lys Arg Ser Trp Phe Gly Asn Phe Ile Ser Leu Asp
        515                 520                 525

Lys Glu Glu Gln Ile Phe Leu Val Leu Lys Asp Lys Pro Leu Ser Ser
        530                 535                 540

Ile Lys Ala Asp Ile Val His Ala Phe Leu Ser Ile Pro Ser Leu Ser
545                 550                 555                 560

His Ser Val Leu Ser Gln Thr Ser Phe Arg Ala Glu Tyr Lys Ala Ser
            565                 570                 575

Gly Gly Pro Ser Val Phe Gln Lys Pro Val Arg Phe Gln Val Asp Ile
            580                 585                 590

Ser Ser Ser Glu Gly Pro Glu Pro Ser Pro Arg Arg Asp Gly Ser Gly
        595                 600                 605

Gly Gly Gly Ile Tyr Ser Val Thr Phe Thr Leu Ile Ser Gly Pro Ser
        610                 615                 620

Arg Arg Phe Lys Arg Val Val Glu Thr Ile Gln Ala Gln Leu Leu Ser
625                 630                 635                 640

Thr His Asp Gln Pro Ser Val Gln Ala Leu Ala Asp Glu Lys Asn Gly
            645                 650                 655

Ala Gln Thr Arg Pro Ala Gly Ala Pro Pro Arg Ser Leu Gln Pro Pro
            660                 665                 670

Pro Gly Arg Pro Asp Pro Glu Leu Ser Ser Ser Pro Arg Arg Gly Pro
        675                 680                 685

Pro Lys Asp Lys Lys Leu Leu Ala Thr Asn Gly Thr Pro Leu Pro
    690                 695                 700
```